United States Patent [19]
Chin-Loy et al.

[11] Patent Number: 5,954,957
[45] Date of Patent: Sep. 21, 1999

[54] MULTI-PURPOSE CAP FOR HYDRAULIC PORTS ON A MEDICAL DEVICE

[75] Inventors: Michael Leon Chin-Loy, Davie; Benjamin Fernandez, Miami, both of Fla.

[73] Assignee: Althin Medical, Inc., Miami Lakes, Fla.

[21] Appl. No.: 08/924,921

[22] Filed: Sep. 8, 1997

Related U.S. Application Data

[63] Continuation of application No. 08/497,528, Jul. 3, 1995, abandoned.

[51] Int. Cl.⁶ .......................... B01D 63/00; B01D 65/02; B65D 41/32
[52] U.S. Cl. ................. 210/232; 210/321.6; 210/321.72; 210/321.69; 604/256; 604/905; 215/307; 215/319; 215/228; 215/321; 215/DIG. 3; 220/287
[58] Field of Search ................... 210/232, 321.6, 210/321.72, 321.69; 604/256, 905; 215/307, 319, 228, 321, DIG. 3; 220/287

[56] References Cited

U.S. PATENT DOCUMENTS

| | | |
|---|---|---|
| 893,469 | 7/1908 | Essmuller . |
| 3,055,363 | 9/1962 | Eckhart .......................... 215/DIG. 3 X |
| 3,092,281 | 6/1963 | Davidson ................................. 215/228 |
| 3,160,269 | 12/1964 | Davidson ............................. 215/228 X |
| 3,189,169 | 6/1965 | Davidson ............................. 215/228 X |
| 3,592,245 | 7/1971 | Schneller et al. .................... 215/228 X |
| 3,987,930 | 10/1976 | Fuson . |
| 4,135,635 | 1/1979 | Fujii et al. . |
| 4,163,722 | 8/1979 | Cosentino . |
| 4,402,420 | 9/1983 | Chernack . |
| 4,432,764 | 2/1984 | Lopez . |
| 4,583,668 | 4/1986 | Maynard, Jr. . |
| 4,886,177 | 12/1989 | Foster . |
| 4,903,855 | 2/1990 | Ducay . |
| 4,969,565 | 11/1990 | Justal et al. . |
| 5,010,928 | 4/1991 | Ballas .................................. 215/228 X |
| 5,015,374 | 5/1991 | Mathieu . |
| 5,413,561 | 5/1995 | Fischell et al. . |

FOREIGN PATENT DOCUMENTS

| | | |
|---|---|---|
| 0 063 640 | 11/1982 | European Pat. Off. . |
| 0 236 033 | 9/1987 | European Pat. Off. . |
| 0 462 355 | 12/1991 | European Pat. Off. . |
| 61-15699 | 10/1982 | Japan . |
| 61-16747 | 1/1986 | Japan . |
| 61-187868 | 8/1986 | Japan . |

OTHER PUBLICATIONS

DIN 58 352, Part 2, "Extracorporeal Circulation; Hemodialysis; Main Dimensions of the Components," Apr. 1983.
DIN 13 090, Part 3, "Kegel und Kegelverbindungen für medinzinische Geräte, Dialysator–Blutanschluss," Apr. 1983, (in German).

*Primary Examiner*—Thomas M. Lithgow
*Attorney, Agent, or Firm*—Klarquist Sparkman Campbell Leigh & Whinston, LLP

[57] ABSTRACT

A cap are disclosed that can be attached to at least two of the following hydraulic fittings found on a medical device: a blood port according to DIN 13 090, part 3, comprising a male DIN nipple and surrounding female threaded collar; a male DIN nipple according to DIN 13 090, part 3; a tapered male barb nipple; and a dialysate port according to DIN 58 352, part 2. When fully attached to one of such ports, the cap serves to maintain an internal condition, such a sterility, of the medical device until time of use. A preferred embodiment of the cap comprises a female receptacle adapted to receive one of the foregoing male nipples, a male projection adapted to be inserted into the dialysate port, a manually grippable portion facilitating manual attachment and detachment of the cap, and a channel or analogous feature defined by the female receptacle for venting of the medical device through the male nipple whenever the cap is fully attached to the male nipple.

32 Claims, 5 Drawing Sheets

MULTI-PURPOSE CAP FOR HYDRAULIC PORTS ON A MEDICAL DEVICE

This application is a continuation of application Ser. No. 08/497,528, filed on Jul. 3, 1995 now abandoned.

FIELD OF THE INVENTION

This invention pertains to caps adapted to fit onto, and thus cover, hydraulic ports of multiple sizes and configurations, particularly such ports on medical devices used for purifying or concentrating biological liquids.

BACKGROUND OF THE INVENTION

A medical device used for the treatment of biological liquids such as blood typically has an active component, such as a semipermeable membrane structure, contained inside a housing or casing. Normally, the biological liquid to be treated is passed into the housing so as to contact one major surface of the membrane, and another liquid is simultaneously passed into the housing so as to contact the other major surface of the membrane, wherein the membrane effects selective transfer of certain liquids and solutes from one liquid to the other through trans-membrane pores. Use of the device normally requires a machine adapted to, inter alia, controllably urge flow of the liquids through the device. Representative medical devices of this type include, but are not necessarily limited to, hemodialyzers, hemoconcentrators, hemofilters, and hemodiafilters.

Hydraulic ports are required in order to effect ingress and egress of liquids into and out of the device, respectively. The ports, generally of a male configuration extending from the housing, are normally dimensioned according to certain standards to ensure hydraulic connectability of the device to machines made by different manufacturers. But, safety reasons (e.g., prevention of accidental misconnection) have resulted in certain ports such as blood ports having very different geometrical profiles than other ports such as dialysate ports.

Since the medical devices are normally sold in a sterile condition, it is considered necessary to provide removable disposable caps for covering the ports from time of manufacture of the device until time for using the device. Contemporary caps are normally made of a molded plastic material suitable for medical applications, but are designed to cover only one type of port.

Prevailing medical economics have urged manufacturers to reduce medical-device manufacturing costs as much as possible. Especially since many medical devices as described above are manufactured using automated methods, there is a significant cost advantage in using as few different parts as possible to make each device. To this end, there is a need for a medical-device cap capable of fitting on ports of different geometries found on the device.

SUMMARY OF THE INVENTION

The present invention meets the foregoing need by providing, inter alia, a cap capable of being attached to at least two of the following hydraulic ports found on medical devices of the type described above:

(a) blood port configured according to DIN 13 090, part 3, comprising a male DIN nipple and surrounding female threaded collar;
(b) male DIN nipple according to DIN 13 090, part 3;
(c) tapered male barb nipple as specified in FIG. 7; and;
(d) dialysate port configured according to DIN 58 352, part 2.

When fully attached to one of the foregoing hydraulic ports so as to cap the port, the cap serves to maintain an internal condition (such as sterility or cleanliness) of the medical device until time of use.

As used herein, "blood" ports are used for introducing into and removing from the medical device the biological fluid (such as extracorporeal blood) to be treated by the device. The "dialysate" ports are used for introducing into and removing from the medical device a liquid used for treating the biological fluid in the device.

To "fully attach" a cap to a port means to insert a male blood nipple into the female receptacle of a cap according to the present invention, or to insert a male projection of a cap according to the present invention into a dialysate port, to the maximal extent the particular port configuration will allow. A fully attached cap serves to maintain an internal condition (such as sterility and/or cleanliness) of the medical device until time of use.

As used herein, a "male blood nipple" encompasses blood ports as specified in DIN 13 090, part 3 (less the threaded female collar), and blood ports as specified in FIG. 7.

According to one aspect of the present invention, the cap comprises a female receptacle capable of receiving at least two of the blood ports listed in (a)–(c), above, so as to fully attach the cap to the respective blood port.

As used herein, the ability of a cap according to the present invention to "receive" a male blood nipple means that the cap can accept the male blood nipple inserted into the female receptacle of the cap sufficiently to fully attach the cap to the male blood nipple.

Caps according to the present invention capable of attachment to dialysate ports according to (d), above, comprise a male projection capable of being removably inserted in a DIN dialysate port according to (d), whenever the female receptacle is not attached to a male blood nipple, sufficiently to fully attach the cap to the dialysate port. Preferably, the male projection and the female receptacle are coaxial with each other but situated on opposite ends of the cap.

According to another aspect of the present invention, the female receptacle of the cap defines a channel that, whenever the cap is fully attached to a male blood nipple, permits venting of the medical device through the male blood nipple while maintaining an internal condition of the medical device until time of use.

According to another aspect of the present invention, the cap comprises a radial extension conforming to threads in the female threaded collar of a blood port according to DIN 13 090 part 3, thereby permitting the cap to be threaded onto the blood port so as to fully attach the cap to the blood port.

In caps according to the present invention that are capable of attaching to blood ports configured according to FIG. 7 (i.e., tapered male barb nipples), the female receptacle of the cap comprises an interior surface defining a ridge adapted to engage the barb, whenever the male nipple is fully inserted into the female receptacle, in a "snap-on" manner. Preferably, the ridge is substantially annular relative to the female receptacle so as to circumferentially engage the barb.

According to another aspect of the present invention, the subject cap further comprises a manually grippable portion that facilitates manual attachment and detachment from a blood port or from a dialysate port.

DETAILED DESCRIPTION OF PREFERRED EMBODIMENTS

A multi-purpose cap according to the present invention is adapted to fit on, and thus cover, any of several types of male hydraulic connection ports normally provided on medical devices such as hemodialyzers, hemofilters, hemodiafilters, and hemoconcentrators. Each device normally has two blood ports (one for liquid input and the other for liquid output) and two dialysate ports (one for liquid input and the other for liquid output). The blood ports are typically dimensioned differently from the dialysate ports to prevent accidental misconnection.

To ensure usability of the medical devices in various countries and regions in the world, the dialysate ports and certain blood ports are normally dimensioned according to internationally recognized standards, as follows:

(a) Blood port: DIN 13 090, part 3.
(b) Dialysate port: DIN 58 352, part 2.

Each of the foregoing standards is incorporated herein by reference.

Figure 7:
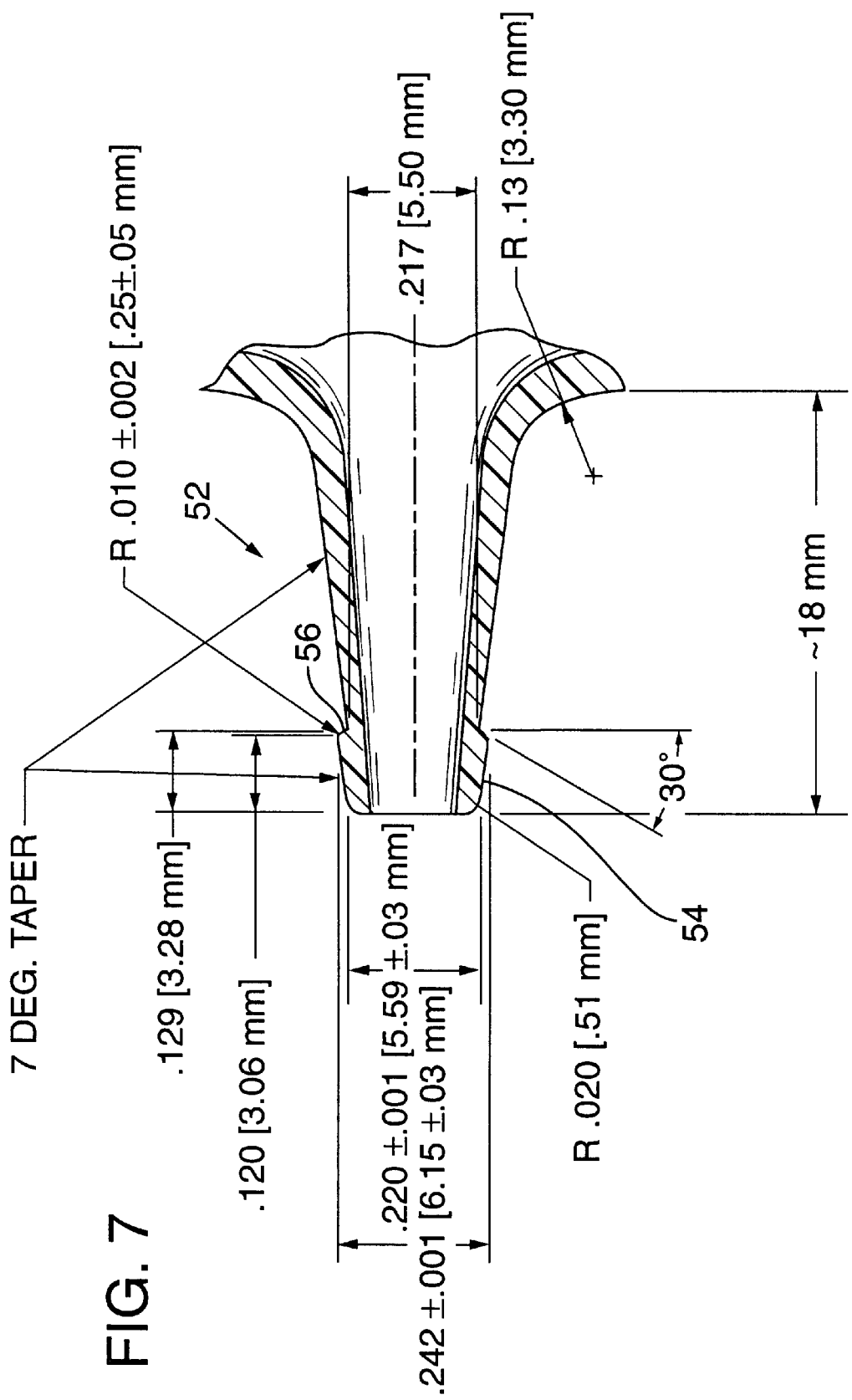
FIG. 7 illustrates, with partial cutaway to show internal detail, an elevational view of a tapered male barb nipple provided as a blood port on certain medical devices, particularly in Japan.

In addition, particularly in Japan, blood ports can have a configuration as illustrated in FIG. 7. The FIG.-7 configuration can be generally described as a tapered male barb nipple.

As used herein: (1) a "DIN blood port" has a tapered male nipple with a surrounding female threaded collar as defined by DIN 13 090, part 3; (2) a "male DIN nipple" is that portion of a DIN blood port exclusive of the female threaded collar; (3) a "JP blood port" has a male profile as depicted in FIG. 7; and (4) a "DIN dialysate port" has a profile as defined by DIN 58 352, part 2. A cap according to the present invention is capable of being attached to at least two of these ports, preferably at least three, and most preferably all four types of ports.

Figure 1:
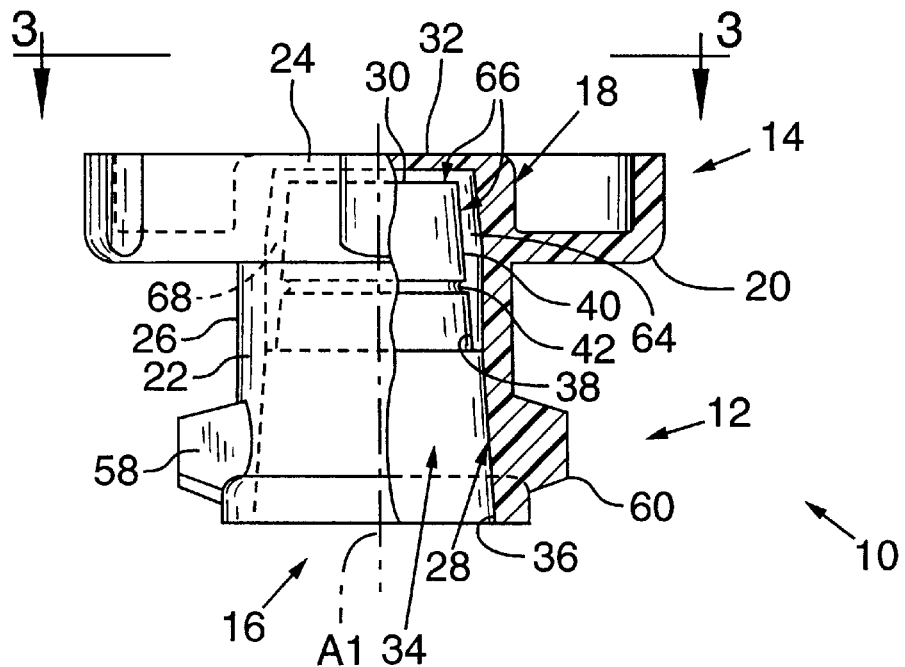
FIG. 1 is an elevational view (with partial cutaway showing internal features) of a preferred embodiment of a cap according to the present invention.

With reference to the drawing, FIG. 1 illustrates a preferred embodiment of a cap 10 according to the present invention. The cap 10 has a longitudinal axis A1, a first end 12, and a second end 14. The first end 12 defines a female portion 16, and the second end 14 defines a male portion 18. Intermediate the first and second ends is a grippable portion 20 adapted to be manually grasped by a user. The female portion 16, the male portion 18, and the grippable portion 20 are preferably, for convenience, coaxial with the axis A1, with the male portion 18 extending in a direction opposite the female portion 16.

Figure 2:
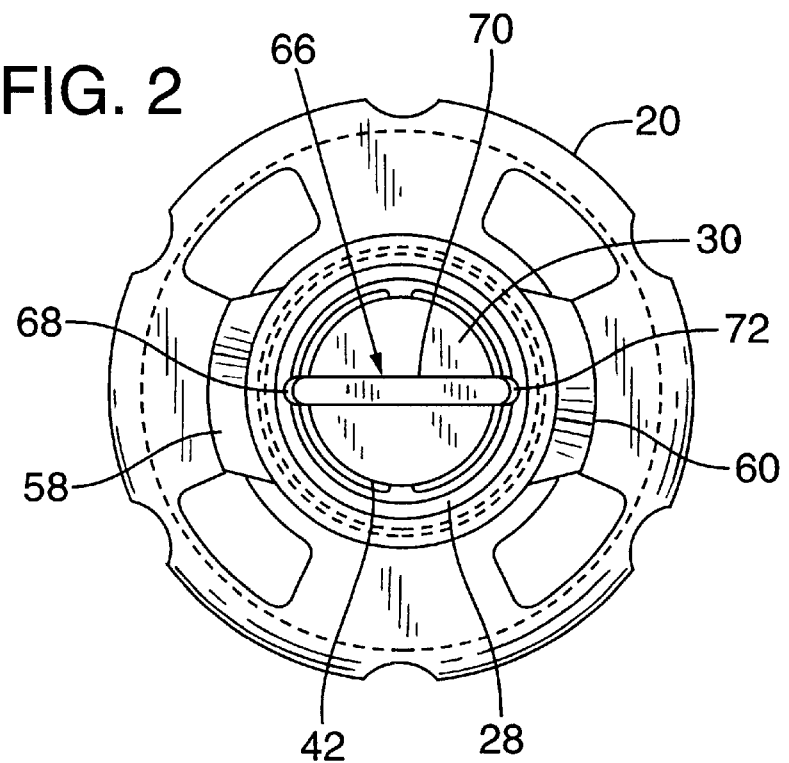
FIG. 2 is an orthogonal plan view of the cap shown in FIG. 1.
Figure 3:
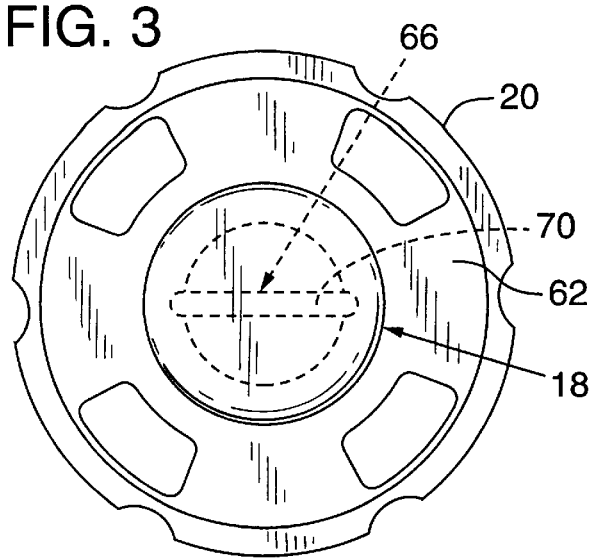
FIG. 3 is an orthogonal plan view, opposite to that of FIG. 2, of the cap shown in FIG. 1.

As shown in FIG. 2, the grippable portion 20 is preferably circumferential relative to the axis A1 for easy grasping by a user particularly whenever the cap must be removed from a port.

According to the preferred embodiment, the female portion 16 is exteriorly cylindrical or frustoconical in profile with a side wall 22 and an end wall 24. The side wall 22 defines an exterior surface 26 and an interior surface 28, and the end wall 24 defines a transverse interior surface 30 and a transverse exterior surface 32. The side wall 22 and end wall 24 cooperatively define a receptacle 34 capable of receiving either a male DIN nipple or a JP blood port, or (preferably) individually both types of ports. As used herein, an ability of the receptacle to "receive" a blood port means that the receptacle 34 is configured to permit the port to be inserted into the receptacle, wherein at least a portion of the interior surface 28 circumferentially conforms to at least a portion of the exterior surface of a male DIN nipple, a JP blood port, or preferably both types of blood ports, respectively. As a result of such conformation, the cap 10 preferably is retained frictionally on the respective blood port whenever the cap 10 is fully attached to the blood port.

To such end, the interior surface 28 of the side wall 22 preferably comprises a proximal tapered region 36, an intermediate region 38, and a distal tapered region 40. Disposed between the intermediate region 38 and the distal tapered region 40 is a ridge 42. Although not required, the ridge 42 is preferably annular in shape.

Figure 4:
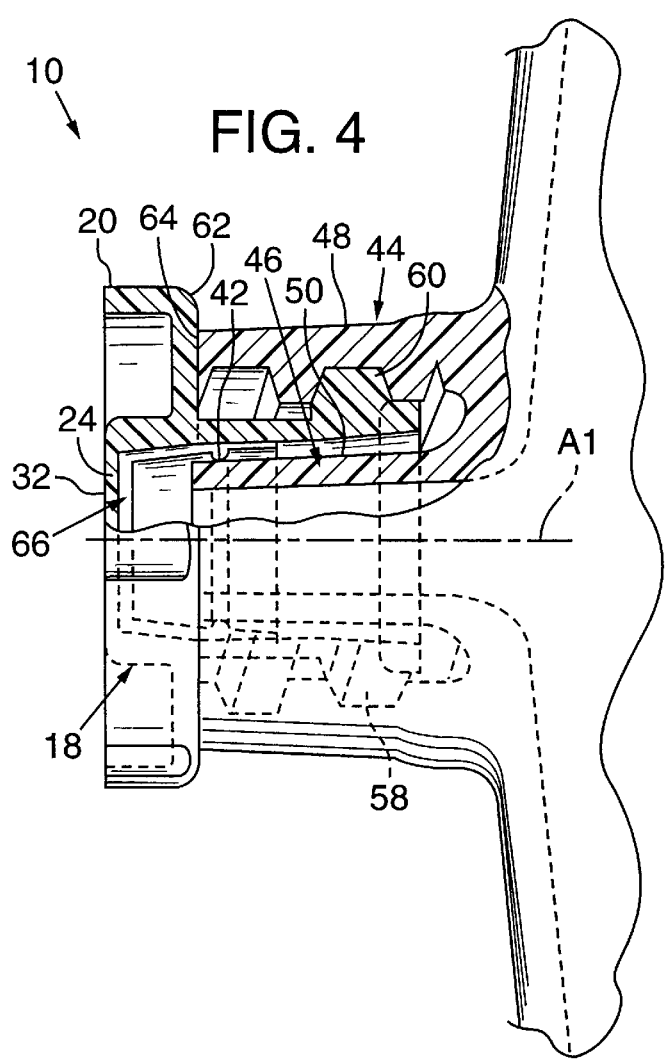
FIG. 4 illustrates, with partial cutaway to show internal details, an elevational view of the cap of FIG. 1 fully attached to a DIN blood port.

FIG. 4 illustrates a cap 10 according to the present invention fully attached to a DIN blood port 44 (shown in dashed outline). As is generally known, the DIN blood port 44 comprises a male DIN nipple 46 coaxially surrounded by a female threaded collar 48. The male DIN nipple 46 is configured as an enlarged "Luer" taper (Luer tapers are generally known in the art) having an exterior frustoconical surface 50. In the receptacle 34, the ridge 42 is adapted to circumferentially engage a portion of the exterior surface 50 of the male DIN nipple 46. Thus, the male DIN nipple 46 can be inserted into the receptacle 34 such that the exterior surface 50 frictionally and circumferentially engages the ridge 42.

Figure 5:
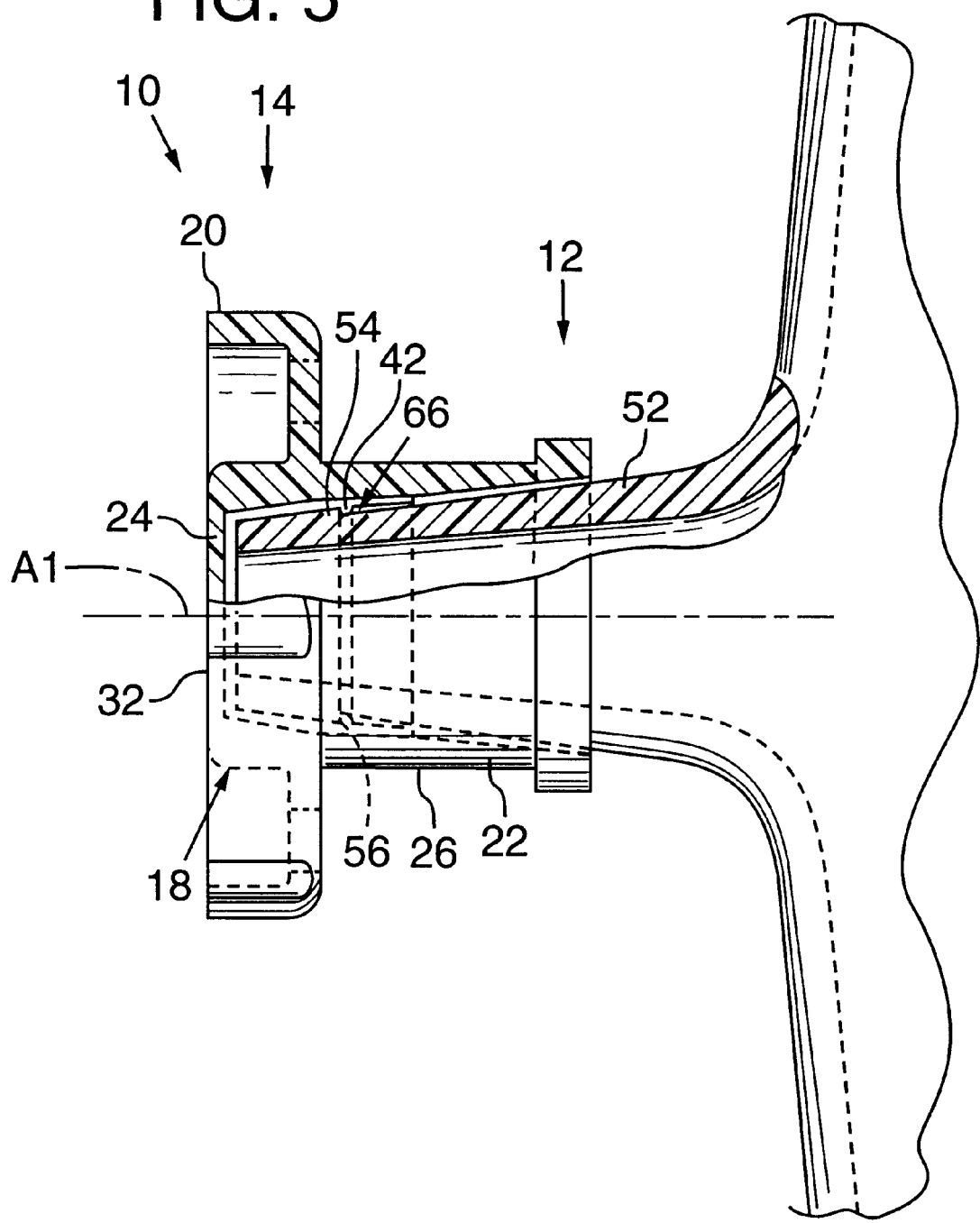
FIG. 5 illustrates, with partial cutaway to show internal details, an elevational view of the cap of FIG. 1 fully attached to a blood port as shown in FIG. 7.

FIG. 5 illustrates a cap 10 according to the present invention fully attached to a JP blood port 52. As discussed above and as shown in FIG. 7, a JP blood port 52 is a type of tapered male barb nipple having a terminal region 54 based with a circumferential escarpment or step 56. Referring again to FIG. 5, the distal tapered region 40 of the cap 10 is adapted to conformably engage the terminal region 54 of the JP blood port 52. Whenever the cap 10 is fully attached to the JP blood port 52 as shown in FIG. 5, the ridge 42 of the cap 10 becomes seated behind the escarpment 56 on the JP blood port 52. Thus, whenever the JP blood port 52 is fully inserted into the receptacle 34, the cap 10 becomes affixed in a "snap-on" manner to the JP blood port 52.

As also shown, for example, in FIGS. 1 and 4, the female portion 16 of the cap 10 preferably includes a pair of diametrically opposing lugs 58, 60 extending radially from the exterior surface 26 and adapted to thread into the female threaded collar 48 of a DIN blood port 44. To attach the cap 10 to a DIN blood port 44, the male DIN nipple 46 is inserted into the receptacle 34 accompanied by manual twisting of the cap 10 relative to the DIN blood port 44 to cause the lugs 58, 60 to thread into the female threaded collar 48. Such threading is continued until substantial resistance is encountered (caused by contact of the underside 62 of the grippable portion 20 with the top edge 64 of the female threaded collar 48), at which time the ridge 42 has become fully engaged against the frustoconical surface 50 of the male DIN nipple 46. Such threading of the cap 10 greatly enhances retention of the cap 10 on the DIN blood port 44. To remove the cap 10, the user merely unthreads it in the opposite direction.

As shown in FIG. 2, the interior surface 28 of the side wall 28 also preferably defines a channel 66. Turning now to FIG. 1, the channel 66 comprises a longitudinal portion 68 extending depthwise into the receptacle 34. The longitudinal portion 68 traverses the area of the interior surface occupied by the ridge 42 and longitudinally spans the distal tapered region 40 toward the end wall 24. The channel 66 preferably also comprises a transverse portion 70 defined by the transverse interior surface 30 of the end wall 24 and contiguous with the longitudinal portion 68. (Most preferably, the channel 66 comprises two opposing longitudinal portions 68, 72 each contiguous with an opposing end of the transverse portion 70. When the cap 10 is fully attached to a blood port of a medical device, the channel 66 permits venting of the interior of the medical device through the blood port during sterilization of the medical device. The channel 66 also provides a "tortuous pathway" from the exterior to the interior of the medical device serving to prevent incursion of microorganisms from the external environment to the interior of the medical device after the device has been sterilized. I.e., in a manner akin to the tapered S-profile of open necks on Pasteur's bottles, sterility of the medical device is maintained even for long periods despite the presence of an air pathway via the channel from the exterior to the interior of the device whenever the caps are fully attached to the blood ports.

Figure 6:
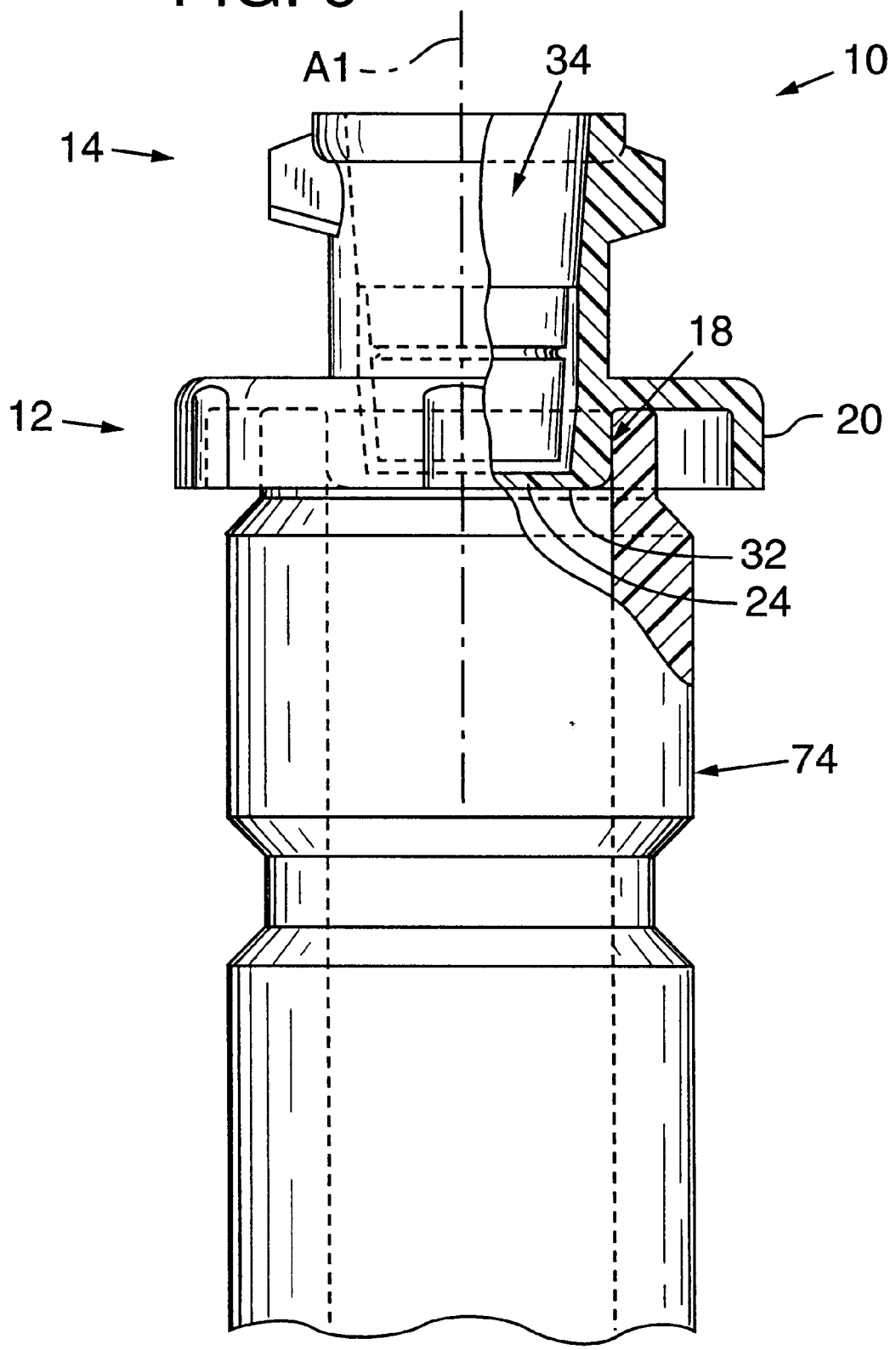
FIG. 6 illustrates, with partial cutaway to show internal details, an elevational view of the cap of FIG. 1 fully attached to a DIN dialysate port.

Turning now to FIG. 6, a cap 10 according to the present invention is shown fully attached to a DIN dialysate port 74. Such attachment is via the male portion 18 of the cap, wherein the male portion 18 is inserted into the lumen of the DIN dialysate port 74. The male portion 18 has a diameter relative to the lumen of the DIN dialysate port permitting substantial frictional engagement of the male portion 18 with the lumen. To detach the cap 10 from the DIN dialysate port 74, the user simply grasps the grippable portion 20 and pulls or twists the cap 10 away from the DIN dialysate port.

The material from which the cap 10 is made is any material that is substantially rigid but with sufficient compliance to frictionally engage the port to which the cap is attached. For example, the cap 10 preferably has sufficient compliance to allow momentary radial deformation, during attachment to a JP blood port, at the moment the annular ridge slides past the escarpment on the JP blood port. The material should also be suitable for medical use: (a) chemical inertness; (b) releases substantially no chemicals, toxins, or residues when in contact with medical liquids; and (c) capable of withstanding conventional methods of sterilization without substantial deterioration, degradation, or deformation. Preferably, the cap is made from any of various polymeric materials ("plastics") suitable for medical use. (In view of the multitudinously different types of medical devices currently available made from polymeric materials, various suitable materials will be apparent to persons of ordinary skill in the art.) Most preferred materials are polyethylene and polypropylene, both of which can be conveniently molded.

A cap according to the present invention permits lower medical-device manufacturing costs because a single type of cap can be used to cover all the hydraulic ports on a medical device. Other benefits include reduction in inventory of different parts, and larger quantity ordering.

The foregoing description has been given by way of non-limiting illustrative example only and it is appreciated that numerous variations may be proposed without departing from the spirit and scope of the invention.

What is claimed is:

1. A cap for capping a port on an extracorporeal blood-treatment device, the cap comprising a female portion comprising attachment means for receiving and attachably engaging a JP blood port on the extracorporeal blood-treatment device or, whenever the cap is not attached to a JP blood port, a DIN blood port, configured according to DIN 13 090 part 3, on the extracorporeal blood-treatment device sufficiently to maintain an internal condition of the extracorporeal blood-treatment device until time for use, the cap further comprising a radial extension from the female portion conforming to threads in a female threaded collar surrounding the male blood nipple of a blood port according to DIN 13 090 part 3 so as to permit the cap to be threaded onto the blood port of DIN 13 090, part 3.

2. A cap for capping a port on an extracorporeal blood-treatment device, the cap comprising a female portion comprising attachment means for receiving and attachably engaging a JP blood port on the extracorporeal blood-treatment device or, whenever the cap is not attached to a JP blood port, a DIN blood port, configured according to DIN 13 090 part 3, on the extracorporeal blood-treatment device sufficiently to maintain an internal condition of the extracorporeal blood-treatment device until time for use, the cap further comprising a male portion extending in a direction opposite the female portion, the male portion comprising means, when the male portion is inserted into a DIN dialysate port, configured according to DIN 58 352 part 2, on the extracorporeal blood-treatment device for attachably engaging the DIN dialysate port sufficiently to maintain an internal condition of the extracorporeal blood-treatment device until time of use.

3. A cap for capping a port on an extracorporeal blood-treatment device, the cap comprising a female portion comprising attachment means for receiving and attachably engaging a JP blood port on the extracorporeal blood-treatment device or, whenever the cap is not attached to a JP blood port, a DIN blood port, configured according to DIN 13 090 part 3, on the extracorporeal blood-treatment device sufficiently to maintain an internal condition of the extracorporeal blood-treatment device until time for use, wherein said attachment means of the female portion comprises an annular ridge situated so as to, whenever the cap is attached to a JP blood port, be situated behind a circumferential escarpment on the JP blood port and, whenever the cap is attached to a DIN blood port, circumferentially engage an external surface of the DIN blood port.

4. A cap according to claim 3, wherein the female portion comprises a side wall having an interior surface defining a channel extending lengthwise along the side wall and through the annular ridge, the channel permitting, whenever the cap is attached to the male blood nipple, venting of the extracorporeal blood-treatment device through the male blood nipple while maintaining the internal condition of the extracorporeal blood-treatment device until time of use.

5. A cap for capping a port on an extracorporeal blood-treatment device, the cap comprising a female portion comprising attachment means for receiving and attachably engaging a JP blood port on the extracorporeal blood-treatment device and, whenever the cap is not attached to a JP blood port, a DIN blood port, configured according to DIN 13 090 part 3, on the extracorporeal blood-treatment device sufficiently to maintain an internal condition of the extracorporeal blood-treatment device until time for use.

6. A cap according to claim 5, further comprising a manually grippable portion radially extending beyond an outer diameter of the female portion, the manually grippable portion facilitating manual attachment and removal of the cap.

7. A cap according to claim 5, further comprising first and second ends, the first end comprising the female portion, and the second end comprising a male projection.

8. A cap according to claim 7, further comprising a manually grippable portion situated between the first and second ends.

9. A cap according to claim 5, wherein the female portion comprises a side wall having an interior surface defining a channel extending lengthwise along the side wall, the channel permitting, whenever the cap is attached to one of said male blood nipples, venting of the extracorporeal blood-treatment device through the male blood nipple while maintaining the internal condition of the extracorporeal blood-treatment device until time of use.

10. A cap according to claim 5, wherein the cap is made entirely from a single unit of material.

11. A cap having a first end and a second end, the first end including a female portion for receiving a male blood nipple on an extracorporeal blood-treatment device so as to maintain, by thus capping said male blood nipple, an internal condition of the extracorporeal blood-treatment device until time of use, the female portion comprising attachment means for receiving and attachably engaging a JP blood port or, whenever the cap is not attached to a JP blood port, a DIN blood port configured according to DIN 13 090 part 3, and the second end comprising a male projection comprising attachment means for attachably engaging, when the male portion is inserted into a DIN dialysate port configured according to DIN 58 352 part 2, the DIN dialysate port, sufficiently to maintain an internal condition of the extracorporeal blood-treatment device until time of use.

12. A cap according to claim 11, wherein said attachment means of the male portion comprises means for sealingly engaging the DIN dialysate port.

13. A cap according to claim 11, further comprising a radial extension from the female portion conforming to threads in a female threaded collar surrounding the male blood nipple of a blood port according to DIN 13 090 part 3 so as to permit the cap to be threaded onto the blood port of DIN 13 090, part 3.

14. A cap according to claim 11, further comprising a manually grippable portion radially extending beyond an outer diameter of the female portion, the manually grippable portion facilitating manual attachment and removal of the cap.

15. A cap according to claim 14, further comprising a radial projection from the female portion conforming to threads in a female threaded collar surrounding the male blood nipple of a blood port according to DIN 13 090 part 3 so as to permit the cap to be threaded onto the blood port of DIN 13 090, part 3.

16. A cap according to claim 15, wherein the radial projection comprises first and second lugs disposed diametrically relative to the female portion.

17. A cap according to claim 11, wherein the cap is made entirely from a single unit of material.

18. A cap according to claim 11, wherein the female portion comprises a side wall having an interior surface defining a channel extending lengthwise along the side wall and through the annular ridge, the channel permitting, whenever the cap is attached to the male blood nipple, venting of the extracorporeal blood-treatment device through the male blood nipple while maintaining the internal condition of the extracorporeal blood-treatment device until time of use.

19. A cap for capping any of multiple types of ports on an extracorporeal blood-treatment device, the cap comprising:

(a) a first end comprising a female receptacle comprising receiving means for individually coaxially receiving a JP blood port nipple and a DIN blood port nipple configured according to DIN 13 090 part 3, the female receptacle further comprising attachment means for attachably engaging the JP blood port nipple or, whenever the cap is not attached to a JP blood port nipple, the DIN blood port nipple sufficiently to maintain an internal condition of the extracorporeal blood-treatment device until time for use; and (b) a second end comprising a male projection comprising attachment means for attachably engaging, when the male portion is inserted into an inside diameter of a DIN dialysate port configured according to DIN 58 352 part 2, the DIN dialysate port sufficiently to maintain an internal condition of the extracorporeal blood-treatment device until time of use.

20. A cap according to claim 19, wherein said receiving means of the female receptacle comprises a side wall having an interior surface with a transverse circular profile, and said attachment means of the female receptacle comprises a ridge situated so as to, whenever the cap is attached to a JP blood port, be situated behind a circumferential escarpment on the JP blood port whenever the JP blood port is fully inserted into the female receptacle.

21. A cap according to claim 20, wherein the ridge is annular and is disposed in the female receptacle so as to circumferentially engage, whenever the male JP blood port nipple is fully inserted into the female portion, the escarpment on the male nipple in a snap-on manner.

22. A cap according to claim 19, further comprising a gripping portion adapted to be manually gripped to facilitate attachment and removal of the cap.

23. A cap according to claim 22, wherein the gripping portion extends radially outward from a location intermediate the first and second ends.

24. A cap according to claim 19, wherein the male portion comprises an external surface having a circular transverse profile having a diameter sufficient to permit the male projection to be coaxially inserted into a DIN dialysate port in a manner by which the external surface frictionally engages a complementary interior surface of the DIN dialysate port.

25. A cap according to claim 19, further comprising a radial projection from the female portion conforming to threads in a female threaded collar surrounding the male blood nipple according to DIN 13 090 part 3 so as to permit the cap to be threaded onto the blood port of DIN 13 090, part 3.

26. A cap according to claim 19, wherein the female portion comprises a side wall having an interior surface defining a channel extending lengthwise along the side wall, the channel permitting, whenever the cap is attached to the male blood nipple, venting of the extracorporeal blood-treatment device through the male blood nipple while maintaining the internal condition of the extracorporeal blood-treatment device until time of use.

27. A cap according to claim 26, wherein the channel comprises a longitudinal portion and a transverse portion contiguous with the longitudinal portion, the longitudinal portion and the transverse portion thus forming a tortuous path through which gases can be cooperatively vented from the extracorporeal blood-treatment device while maintaining an internal condition of the extracorporeal blood-treatment device until time of use.

28. A cap for capping any of multiple types of ports on an extracorporeal blood-treatment device, the cap comprising:

(a) a first end comprising a female portion comprising receiving means for individually receiving a blood port nipple selected from a group consisting of a JP blood port nipple and a DIN blood port nipple configured according to DIN 13 090 part 3, said receiving means comprising a longitudinally extending interior surface having a circular transverse section and comprising a proximal tapered region and a distal tapered region, the distal tapered region being dimensioned so as to be complementary to a terminal portion of a JP blood port nipple; and (b) the female portion also comprising attachment means for circumferentially engaging a DIN blood port nipple, said attachment means comprising an annular ridge disposed between the distal and proximal tapered regions, the annular ridge (1) circumferentially engaging the DIN blood port nipple whenever such a DIN blood port nipple is fully inserted into the female receptacle, and (2) circumferentially engaging, in a snap-on manner, an escarpment adjacent the terminal portion of the JP blood port nipple whenever such a JP blood port nipple is fully inserted into the female receptacle, so as to maintain, whenever the blood port is so capped, an internal condition of the extracorporeal blood-treatment device until time of use.

29. A cap according to claim 28, further comprising a second end oriented oppositely but coaxially with the first end, the second end defining a substantially cylindrical male projection capable of being inserted into an opening of a dialysate port configured according to DIN 58 352 part 2.

30. A cap for capping any of multiple types of ports on an extracorporeal blood-treatment device, the cap comprising:
   (a) receptacle means for receiving a male blood port nipple on the extracorporeal blood-treatment device, the male blood port nipple being selected from a group consisting of a JP blood port nipple and a DIN blood port nipple; and
   (b) a male projection extending in a direction opposite said receptacle means, the male projection having a circular transverse section having a diameter sufficient for insertion of the male projection into a DIN dialysate port on the extracorporeal blood-treatment device so as to removably attach the cap to the DIN dialysate port and maintain an internal condition of the extracorporeal blood-treatment device until time for use.

31. The cap according to claim 30, wherein the cap is made entirely from a single unit of material.

32. The cap according to claim 30, wherein said receptacle means comprises a side wall having an interior surface defining a channel extending lengthwise along the side wall, the channel permitting, whenever the cap is attached to the male blood nipple, venting of the extracorporeal blood-treatment device through the male blood nipple while maintaining the internal condition of the extracorporeal blood-treatment device until time of use.

* * * * *